US012303463B2

(12) United States Patent
Ariagno et al.

(10) Patent No.: US 12,303,463 B2
(45) Date of Patent: May 20, 2025

(54) FEMALE-FEMALE ADAPTER

(71) Applicant: TAKEDA PHARMACEUTICAL COMPANY LIMITED, Osaka (JP)

(72) Inventors: Scott Richard Ariagno, Inverness, IL (US); Mark Schilling, Mundelein, IL (US); Amey Mathakari, Mundelein, IL (US); Daniel Sanchez, Round Lake Beach, IL (US); Christopher Blackledge, McHenry, IL (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 653 days.

(21) Appl. No.: 17/258,833

(22) PCT Filed: Jul. 11, 2019

(86) PCT No.: PCT/US2019/041354
§ 371 (c)(1),
(2) Date: Jan. 8, 2021

(87) PCT Pub. No.: WO2020/014447
PCT Pub. Date: Jan. 16, 2020

(65) Prior Publication Data
US 2021/0290486 A1    Sep. 23, 2021

Related U.S. Application Data

(60) Provisional application No. 62/697,677, filed on Jul. 13, 2018.

(51) Int. Cl.
*A61J 1/20* (2006.01)
(52) U.S. Cl.
CPC ........... *A61J 1/2048* (2015.05); *A61J 1/2096* (2013.01)

(58) Field of Classification Search
CPC .... A61J 1/2048; A61J 1/2096; A61J 2200/76; A61J 1/1406; A61J 1/2013; A61J 1/2055;
(Continued)

(56) References Cited

U.S. PATENT DOCUMENTS

| 6,558,365 B2 | 5/2003 | Zinger et al. |
| 2007/0150054 A1* | 6/2007 | Pynson ................. A61F 2/1664 623/6.12 |

(Continued)

FOREIGN PATENT DOCUMENTS

| EP | 856331 A2 * | 8/1998 | ............ A61J 1/2096 |
| WO | 2009/090627 A1 | 7/2009 | |

OTHER PUBLICATIONS

Extended European Search Report issued with corresponding European Patent Application No. 19833411.2 dated Mar. 15, 2022.
(Continued)

*Primary Examiner* — Susan S Su
*Assistant Examiner* — Katherine-Ph Minh Pham
(74) *Attorney, Agent, or Firm* — Troutman Pepper Locke LLP

(57) ABSTRACT

The invention is directed to a female-female syringe adapter, related systems, and methods of using the female-female adapter. The female-female syringe adapter may be used with male nozzles of syringes and reconstitution devices when reconstituting a lyophilized powder. The female-female adapter also may be used to combine doses in a common syringe from mixed reconstitution products in a multi-chambered syringe.

11 Claims, 22 Drawing Sheets

(58) Field of Classification Search
CPC .. A61M 2005/3114; A61M 2039/1077; A61M 2205/75; A61M 2209/06
See application file for complete search history.

(56) References Cited

U.S. PATENT DOCUMENTS

| | | | |
|---|---|---|---|
| 2010/0160889 A1* | 6/2010 | Smith | A61J 1/2096 |
| | | | 604/414 |
| 2012/0022457 A1 | 1/2012 | Silver | |
| 2013/0105018 A1 | 5/2013 | Sherman et al. | |
| 2013/0178804 A1* | 7/2013 | Tennican | A61M 39/20 |
| | | | 604/218 |
| 2014/0311624 A1* | 10/2014 | Eilertsen | A61J 1/2096 |
| | | | 141/18 |
| 2015/0126958 A1 | 5/2015 | Sanders et al. | |
| 2015/0250680 A1* | 9/2015 | Browka | A61J 1/2096 |
| | | | 604/406 |
| 2016/0339226 A1* | 11/2016 | Sealfon | A61M 39/1011 |
| 2016/0367439 A1* | 12/2016 | Davis | A61J 1/2096 |
| 2018/0008812 A1* | 1/2018 | Roxas | A61M 1/367 |

OTHER PUBLICATIONS

International Search Report and Written Opinion issued in corresponding International Application No. PCT/US19/41354 date Nov. 18, 2019.
Office Action issued with corresponding Chinese Patent Application No. 201980046162.X dated Nov. 25, 2023 (including English Translation).

* cited by examiner

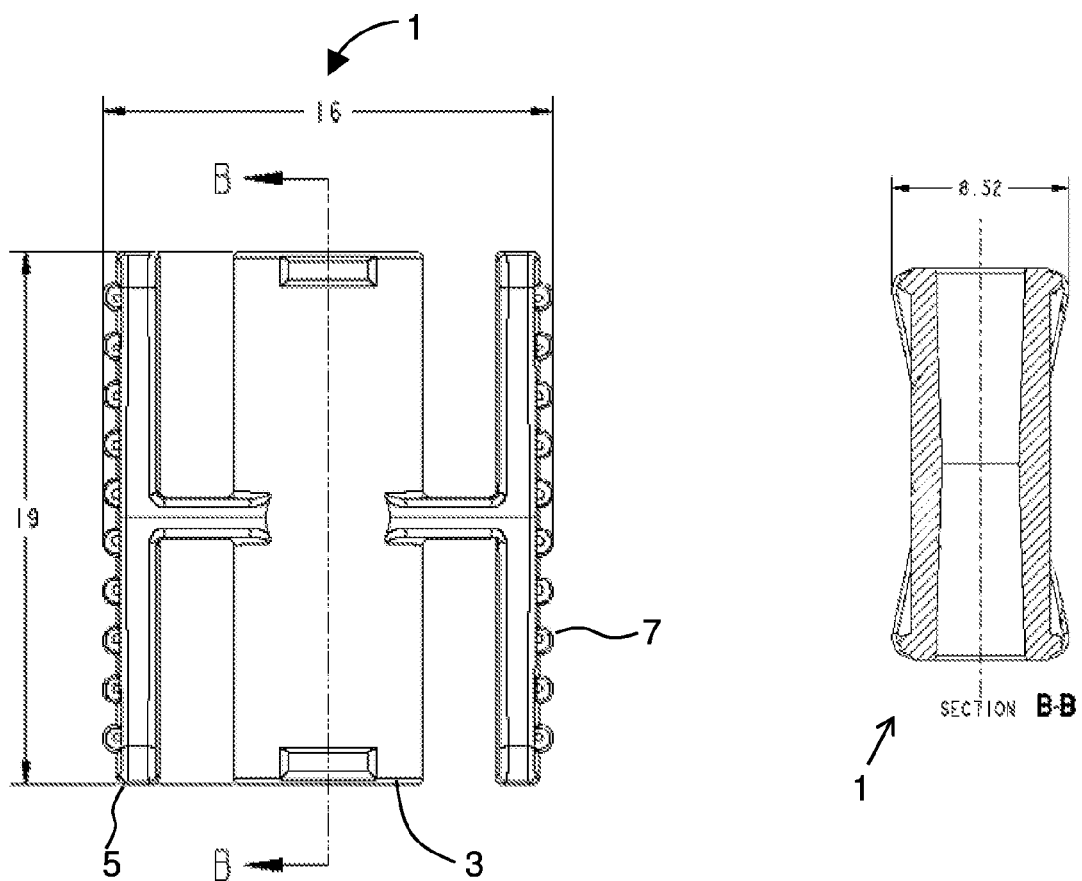
FIG. 3
FIG. 4
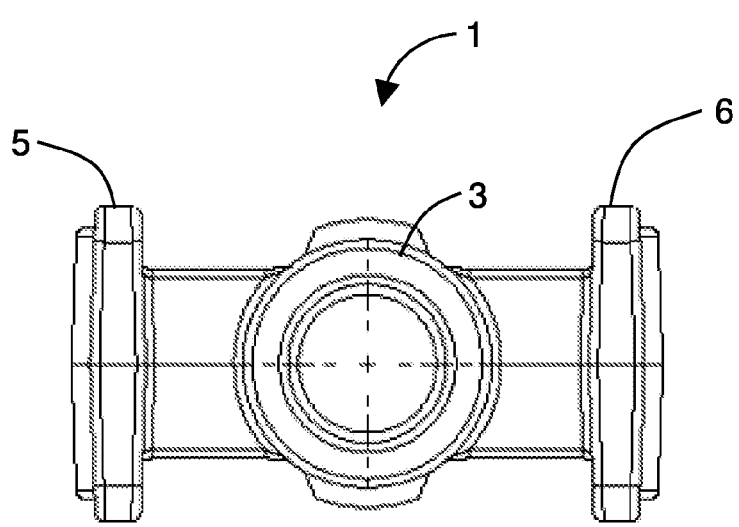
FIG. 5

SECTION B-B

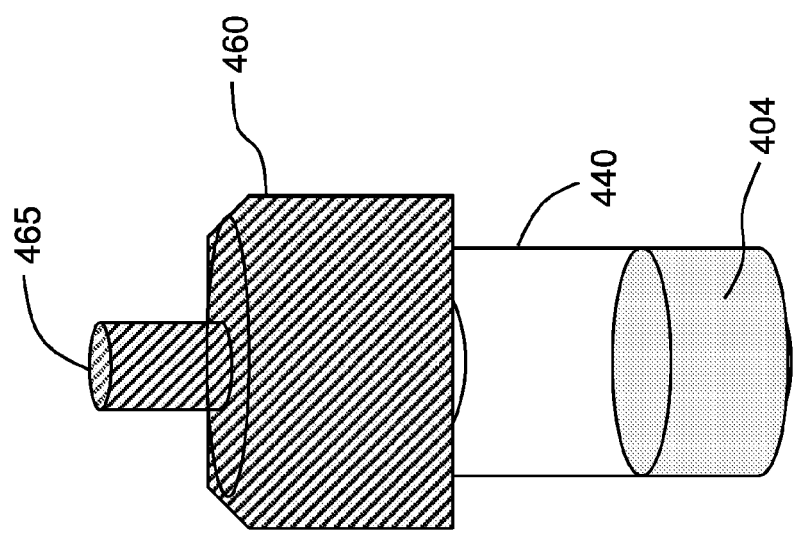
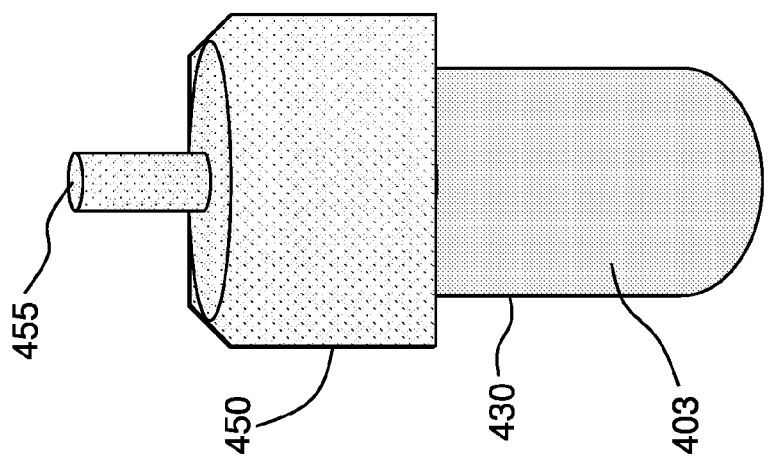
FIG. 25

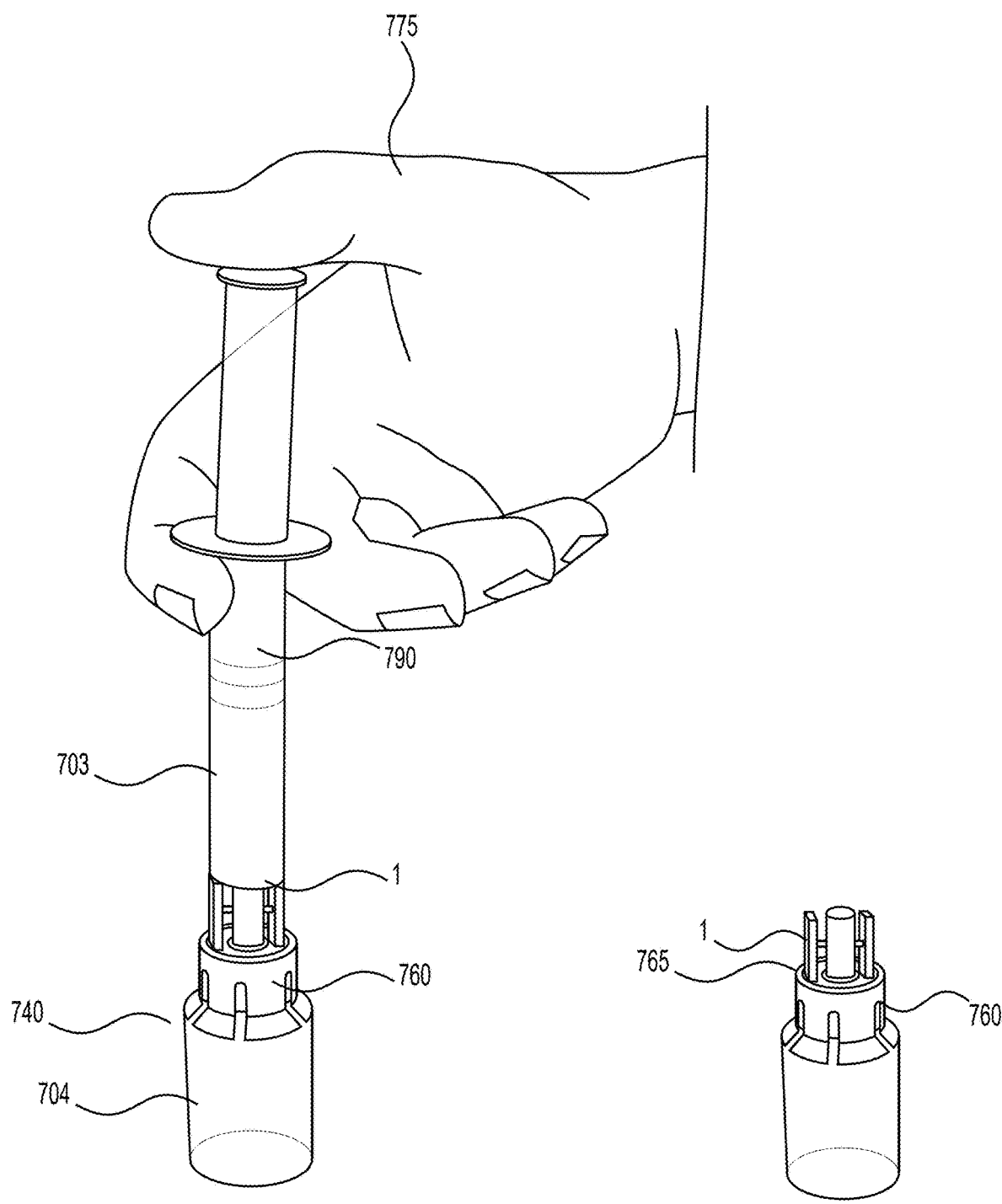
*FIG. 32*  *FIG. 33*

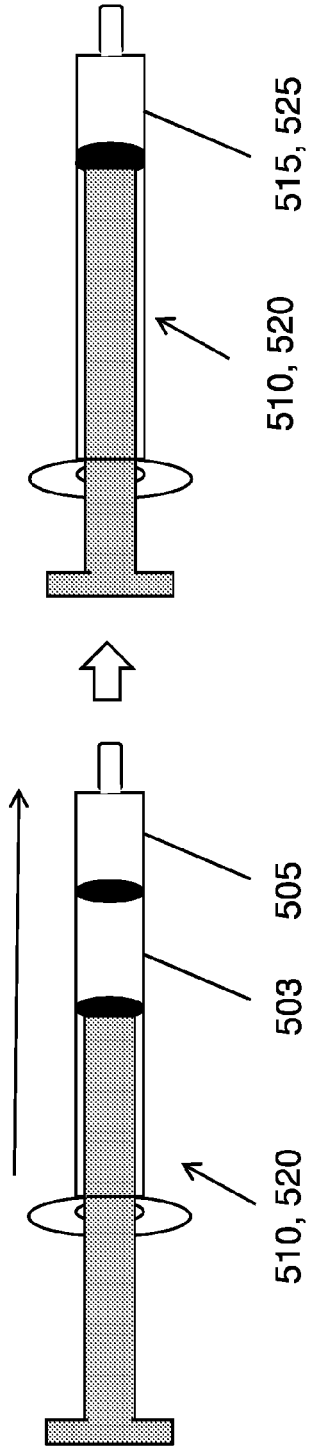
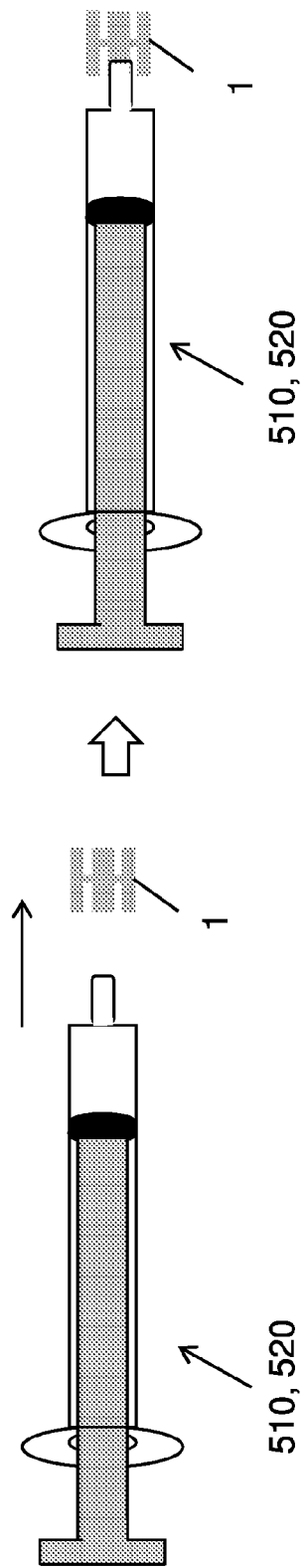
FIG. 35
FIG. 36

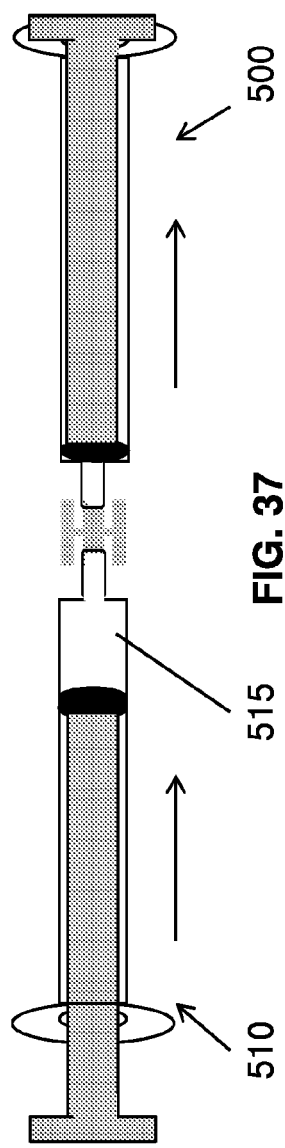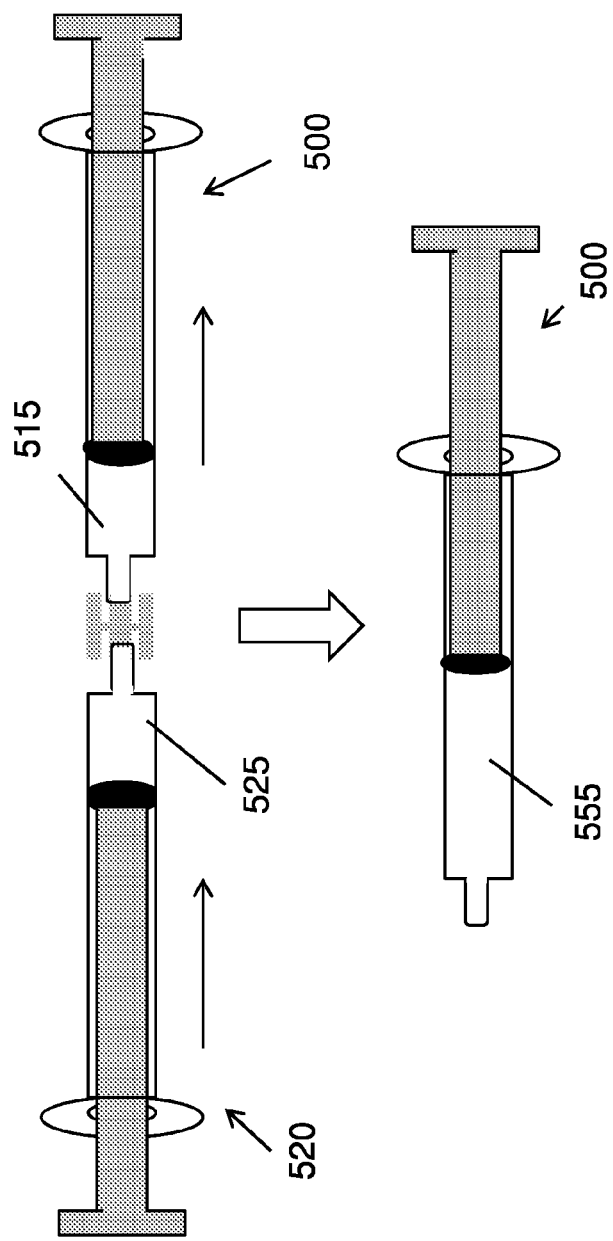

FEMALE-FEMALE ADAPTER

CROSS REFERENCE TO RELATED APPLICATIONS

This application is a national stage application of International Application No. PCT/US2019/041354, having an international filing date of 11 Jul. 2019, which claims the benefit of U.S. Provisional Application No. 62/697,677, filed 13 Jul. 2018, both of which are incorporated herein in their entirety as if fully set forth below.

TECHNICAL FIELD

The disclosure relates to adapters, particularly female-female adapters for connection to male nozzles.

BACKGROUND

To remain effective, certain drugs must be stored in powdered form until use. Once mixed into a solution, these drugs rapidly lose effectiveness. As such, the powdered drugs are reconstituted, or mixed with a liquid, just before administering to a subject. However, the reconstitution process can be confusing and difficult, regardless of whether the reconstitution process is carried out by a healthcare profession or an individual at home. If problems arise when reconstituting the drugs, the subject is left with an expensive product that cannot be used. Current reconstitution devices and methods are not failsafe, leading to expensive, unusable doses of reconstituted drugs.

SUMMARY

The present invention provides a female-female adapter for use with reconstitution devices when an issue arises during the reconstitution process. As such, users still are able to achieve full diluent transfer despite such issues and avoid wasting the reconstitution product.

During reconstitution, the reconstitution product comprises one vial containing lyophilized powder (the drug) and another vial containing a diluent for mixing with the lyophilized powder. A reconstitution device is a mechanism used to transfer the diluent to mix with the lyophilized powder when reconstituting the product. A common problem with reconstitution devices is recovery of the product from incomplete diluent transfer during reconstitution. Users who perform two vial drug/biologic reconstitutions by center-disconnecting double spike reconstitution devices struggle to achieve full diluent transfer to the lyophilized products for various reasons. Users may be patients, caregivers, nurses, or pharmacists.

For example, the spikes of a reconstitution device must pierce straight through a septum in each vial for reliable penetration. Angled insertion may break/bend the spike, and the spike lumen may remain occluded by stopper material. Further, improper vial orientation may be problematic. Vials must engage correct sides of the reconstitution device, i.e. spike water first, assuming correct packaging. Vials must be in the proper orientation at time of spiking and throughout duration of fluid transfer. In addition, internal seals in the reconstitution device (i.e. male-female Luer engagement) must remain tightly connected to prevent loss of vacuum upon spiking. Users can damage the seal by torqueing in either direction. Another problem that arises during the reconstitution process relates to inadequate vacuum in the lyophilized product vial, which leads to lack of power when attempting to pull all of diluent into the vial. Multiple scenarios could result in inadequate vacuum.

The present invention provides an easy-to-use solution to the various diluent transfer issues arising during the reconstitution process. By packaging a female-female adapter with the reconstitution device, the invention proactively provides a solution, should a diluent transfer issue arise. The female-female adapter is sized to fit within reconstitution device packaging and can be sterilized at the same time as the reconstitution device. The female-female adapter allows connection of the adapter to a male nozzle, which may be the male nozzle of the reconstitution device, the male nozzle of a syringe, or connection of respective male nozzles of two syringes.

In an embodiment, the present invention provides a female-female adapter. The female-female adapter comprises a central lumen, wings, and a filter. The central lumen has two ends, an inner surface, and an outer surface. The two ends are opposite each other in a longitudinal direction. Each of the two ends is capable of interlocking with a male end of a nozzle. In certain embodiments, the male end of the nozzle is a Luer-lock.

The central lumen has a central portion in the longitudinal direction. The wings extend from the central portion and are located at points opposite each other around a circumference of the central lumen. Each wing forms a slat parallel to the central lumen, the slat having a first end and a second end wider than a middle of the slat. This creates a "bowtie" configuration. In an aspect, the wings comprise ridges on a surface of the slat exterior to the central lumen. The ridges allow for better grip for a user.

The filter is disposed in the central lumen at the central portion and perpendicular to the longitudinal direction of the central lumen. Any suitable means may be used to dispose the filter within the central lumen. As an example, the filter may be welded to the central lumen.

In an embodiment, the present invention provides a system for a reconstitution product. The system comprises a reconstitution device and a female-female adapter. In certain embodiments, the system further comprises a reconstitution product. The reconstitution device comprises a first component and a second component, the first component and the second component capable of disconnecting. The female-female adapter comprises wings extending from a central lumen, the female-female adapter having a first end connectable with a male nozzle of a syringe and a second end connectable with a male nozzle of the first component or the second component. The reconstitution product comprises a first vial comprising a diluent and a second vial comprising a lyophilized powder, the first vial for connecting to the first component and the second vial connecting to the second component.

The system may further comprise a package comprising the reconstitution device and the female-female adapter. Within the package, the female-female adapter is arranged in a space between the reconstitution device and an inside surface of the package, the wings releasably interlocking with the inside surface of the package. In certain embodiments, the package is a blister pack. A blister pack is a type of packaging with pre-formed blisters or pockets where a product sits in place within the package. A backing is typically sealed to the blister pack to secure the product. In certain embodiments, the package and contents are sterilized. Certain embodiments of the system further comprise including the reconstitution product in the system with the reconstitution device package.

In an embodiment, the present invention provides a method of using a female-female adapter to reconstitute a lyophilized powder. A syringe is attached to a first component of a reconstitution device and disconnecting the syringe after extracting a diluent from a first vial. A lyophilized powder is reconstituted by attaching the male nozzle of the syringe to a first end of a female-female adapter, attaching a second end of the female-female adapter to a male nozzle of a second component of a reconstitution device attached to a second vial comprising the lyophilized powder, and ejecting the diluent into the second vial. In certain embodiments of the methods, the syringe has a male Luer lock nozzle.

In an embodiment, the present invention provides a method of using a female-female adapter to reconstitute a lyophilized powder. A first end of a female-female adapter is attached to a male nozzle of a syringe. In certain embodiments of the methods, the syringe has a male Luer lock nozzle. A second end of the female-female adapter is attached to a first component of a reconstitution device attached to a first vial, a diluent is extracted from the first vial into the syringe, and the syringe is disconnected from the female-female adapter. A lyophilized powder is reconstituted by attaching the male nozzle of the syringe to a second component of the reconstitution device attached to a second vial comprising the lyophilized powder and ejecting the diluent into the second vial.

In an aspect of the invention, the female-female adapter is attached without touch contamination. The ridges on the wings provide an area for a user to securely grip the adapter without contaminating the central lumen.

In an embodiment, the present invention provides a system for a reconstitution product comprising a reconstitution device and a female-female adapter. The reconstitution device comprises a plunger and a dual-chambered syringe comprising first chamber containing a diluent and a second chamber containing a lyophilized powder. The female-female adapter comprises wings extending from a central lumen. The female-female adapter has a first end connectable with a male nozzle of the dual-chambered syringe a second end connectable with a male nozzle of a syringe.

In an embodiment, the present invention provides a method of using a female-female adapter for dose combination. A first end of a female-female adapter is attached to a male nozzle of a syringe. A first dose and a second dose are combined in the syringe by an extraction process. The extraction process comprises extracting the doses from two multi-chambered syringes. A second end of the female-female adapter is attached to a male nozzle of a first multi-chambered syringe, and the female-female adapter is disconnected from the first multi-chambered syringe after extracting and collecting the first dose in the syringe. The second end of the female-female adapter is attached to a male nozzle of a second multi-chambered syringe, and the female-female adapter is disconnected from the second multi-chambered syringe after extracting and collecting the second dose in the syringe.

BRIEF DESCRIPTION OF THE DRAWINGS

FIG. 3 shows a side view of the female-female adapter.
FIG. 4 shows a cross-section section of a side view of the female-female adapter.
FIG. 5 shows a top view of the female-female adapter.
FIG. 25 shows the reconstitution device components attached to the reconstitution product vials.
FIG. 32 shows a user manually transferring diluent from the syringe into a vial containing lyophilized powder.
FIG. 33 shows the adapter docked to the male Luer fitting of a component of a reconstitution device.

FIG. 35 shows reconstitution of a product in a dual-chambered syringe.

FIG. 36 shows attachment of the female-female adapter to the dual-chambered syringe.

FIG. 37 shows collection of a reconstituted dose from the dual-chambered syringe into a collection syringe using the female-female adapter.

FIG. 38 shows pooling of reconstituted doses into a collection syringe using the female-female adapter.

DETAILED DESCRIPTION

Figure 1:
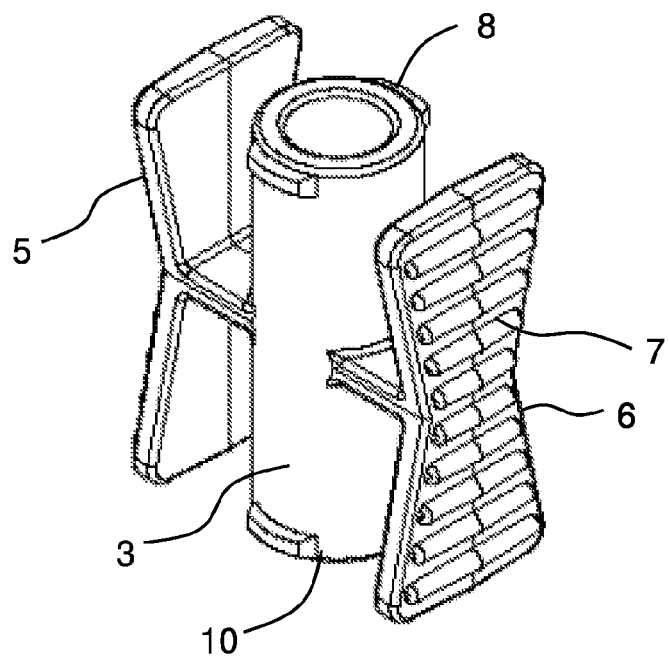
FIG. 1 shows a perspective view of an embodiment of the female-female adapter.

A common problem with reconstitution devices is recovery from incomplete diluent transfer during product reconstitution. Users who encounter issues with full diluent transfer may include patients, caregivers, nurses, and pharmacists. The product reconstitution may involve two vial drug/biologic reconstitutions. The reconstitution device may be a center-disconnecting double spike device. Examples of such reconstitution devices include MIX2VIAL® (a registered United States trademark of Medimop Medical Projects Ltd., manufactured by West Pharma. Services IL, Ltd., a subsidiary of West Pharmaceutical Services, Inc.) and NEXTARO® (a registered European Union trademark, manufactured by sfm medical devices GmbH). When using this type of device, a small percentage of users struggle to achieve full diluent transfer to the lyophilized products for various reasons.

Furthermore, different failure modes can result in no diluent transfer or partial diluent transfer. The vials may be spiked in the wrong order. In such a case, the vials would be pierced by opposite spikes than the reconstitution device intended. In another example, the vials may be spiked in the wrong orientation, i.e., the vial containing the lyophilized powder may not be sitting upright on a surface such as a table when pierced.

Failures can be avoided by adhering to a careful technique and following instructions for use precisely. However, male Luer syringes cannot connect directly to vial adapters with male Luer ports. As such, users have limited options to recover from subtle deviations from instructions for use with reconstitution devices such as MIX2VIAL® and NEXTARO®. One option is to discard the expensive lyophilized biologic product or reconstitution product. The user may try again with new vials, resulting in delayed therapy, or skip therapy altogether. In a second option, the user may remove the reconstitution device, obtain a sterile needle (not included), and manually move fluids by needle and syringe. However, vial capture features in present NEXTARO® and MIX2VIAL® reconstitution devices make vials difficult or impossible to remove in a safe manner. Further, the workaround in the second option results in a lack of product filtering and elevates the risk of needle-stick injury, stopper coring/fragmentation, and touch contamination.

The present invention enables recovery of the reconstituted product when diluent transfer issues arise. The present invention provides a customized female-female adapter, which may be a female-female Luer adapter, which may be conveniently packaged with the reconstitution device. The female-female adapter presents a new option for recovery from many failure modes, without increasing package size or adding additional packaging for reconstitution devices such as MIX2VIAL® and NEXTARO®. The female-female adapter may be captured in the base of a package for the reconstitution device. For example, the package may be a thermoformed or molded blister tray packaging or a blister pack. Extruded wings around the female-female adapter create additional points to anchor the device to the packaging. The female-female adapter should be secured tightly enough to prevent accidental detachment during shipping and handling.

FIG. 1 through FIG. 5 show an embodiment of the female-female adapter 1.

FIG. 1 shows a perspective view of an embodiment of the female-female adapter.

Figure 2:
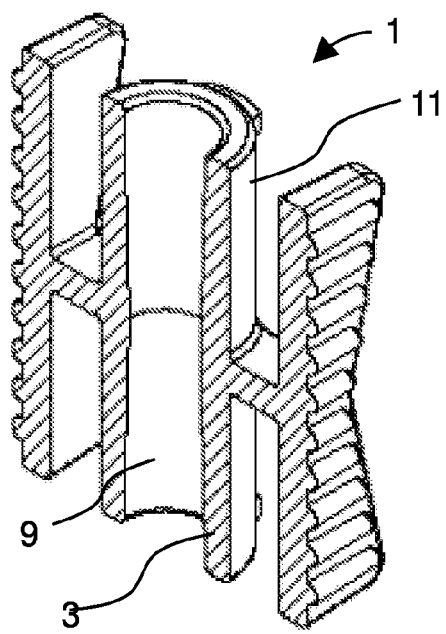
FIG. 2 shows a perspective view of the cross-section of the female-female adapter.

FIG. 2 shows a perspective view of the cross-section of the female-female adapter. FIG. 3 shows a side view of the female-female adapter.

FIG. 4 shows a cross-section section of a side view of the female-female adapter.

FIG. 5 shows a top view of the female-female adapter. As shown, the female-female adapter 1 has a central lumen 3 and wings 5 and 6. The central lumen has two ends 8 and 10, an inner surface 9, and an outer surface 11. The two ends are opposite each other in a longitudinal direction. Each of the two ends is capable of interlocking with a male nozzle.

The central lumen has a central portion in the longitudinal direction. The wings 5 and 6 extend from the central portion and are located at points opposite each other around a circumference of the central lumen. Each wing 5 and 6 forms a slat parallel to the central lumen 3, the slat having a first end and a second end wider than a middle of the slat. This creates a bow-tie configuration. In an aspect, the wings 5 and 6 comprise ridges 7 on a surface of the slat exterior to the central lumen. The ridges 7 allow for better grip for a user.

In certain embodiments, the female-female adapter may have one, two, three, or four wings. In preferred embodiments, the female-female adapter has two wings. Optionally, the wings could comprise revolved protrusions instead of linear extrusions. Adjusting the wing configuration may provide enhanced ability to prevent touch contamination or to correctly self-align a syringe during connection.

FIGS. 3, 4, 8, 13, and 14 show dimensions of the female-female adapter. In preferred embodiments, a height of the female-female adapter is 19 mm, a width of the adapter from one wing to the other is 16 mm, and wing depth is 8.52 mm. As shown in the embodiment in FIG. 14, a preferred dimension of an expanded central portion 25 of the central lumen has a diameter of 15 mm. The adapter height was selected to fit height available within typical reconstitution device packages, with little to no increase (<10 mm) in package size, so that one adapter size can be used with either MIX2VIAL® or NEXTARO®.

The female-female adapter may comprise a filter 20 disposed in the central lumen 3, as shown in FIG. 8 through FIG. 17. Any suitable means may be used to dispose the filter 20 within the central lumen 3. As an example, the filter may be welded to the central lumen. The filter may be welded, mechanically captured, heat staked, or pressed into the adapter fluid path to remove particulates, aggregates, or biologic filaments as fluid transfers through the adapter. The filter 20 is disposed in the central lumen 3 at the central portion and perpendicular to the longitudinal direction of the central lumen. The filter may be formed from any suitable material. For example, the filter may be a polyester filter. In an embodiment, the pore size of the filter may be 0.2 to 150 microns. In another embodiment, the pore size of the filter may be 11 to 51 microns. In an embodiment, the filtration area may be about 0.05 cm2 and fit within a standard female Luer fitting.

Figure 11:
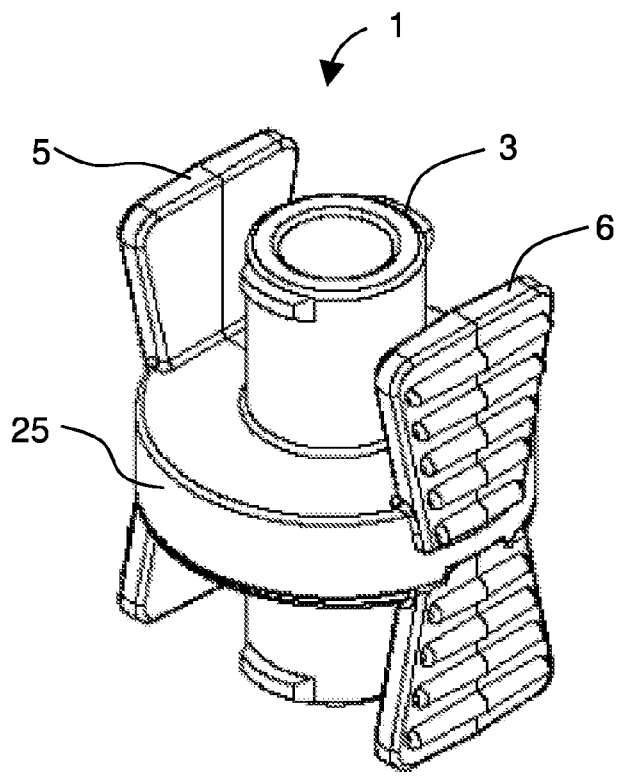
FIG. 11 shows a perspective view of an embodiment of the female-female adapter.

FIG. 11 shows a perspective view of an embodiment of the female-female adapter.

Figure 12:
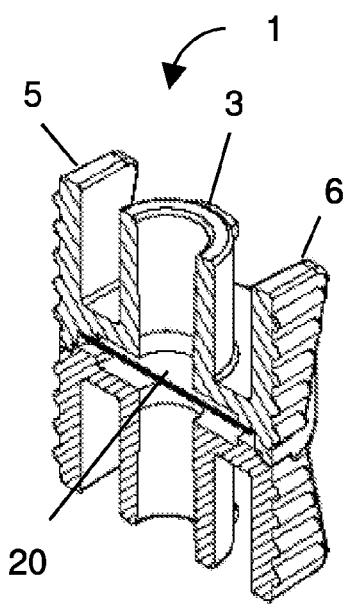
FIG. 12 shows a perspective view of the cross-section of an embodiment of the female-female adapter.

FIG. 12 shows a perspective view of the cross-section of an embodiment of the female-female adapter.

Figure 13:
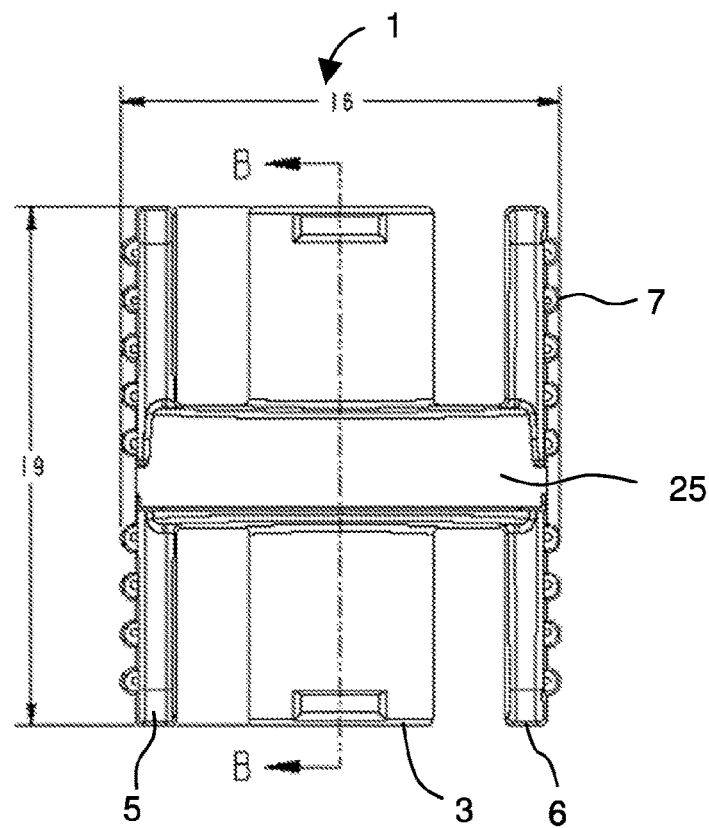
FIG. 13 shows a side view of the female-female adapter.

FIG. 13 shows a side view of the female-female adapter.

Figure 14:
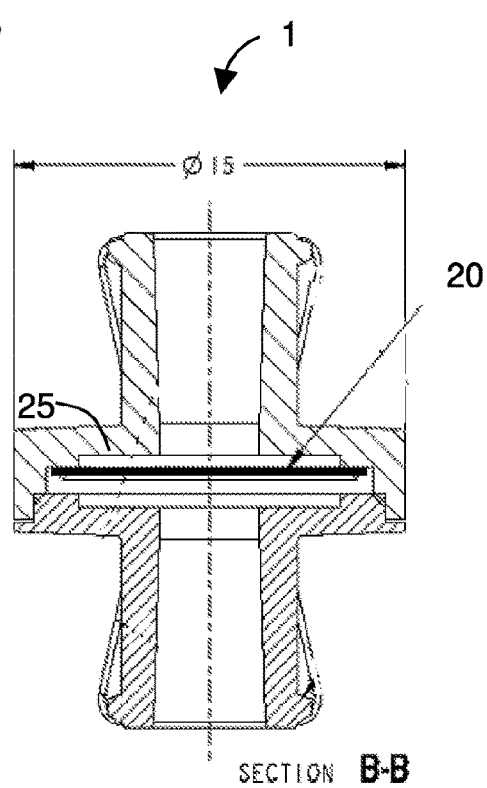
FIG. 14 shows a cross-section section of a side view of the female-female adapter.

FIG. 14 shows a cross-section section of a side view of the female-female adapter.

Figure 15:
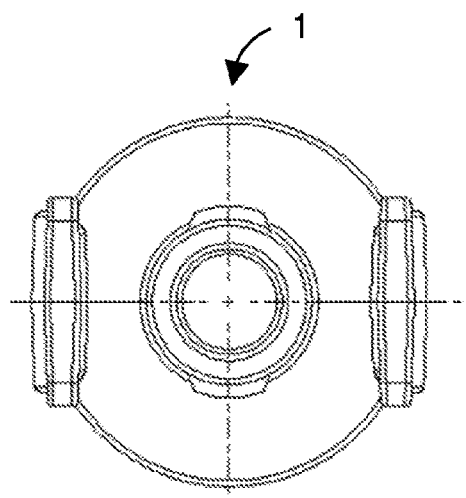
FIG. 15 shows a top view of the female-female adapter.

FIG. 15 shows a top view of the female-female adapter.

Figure 16:
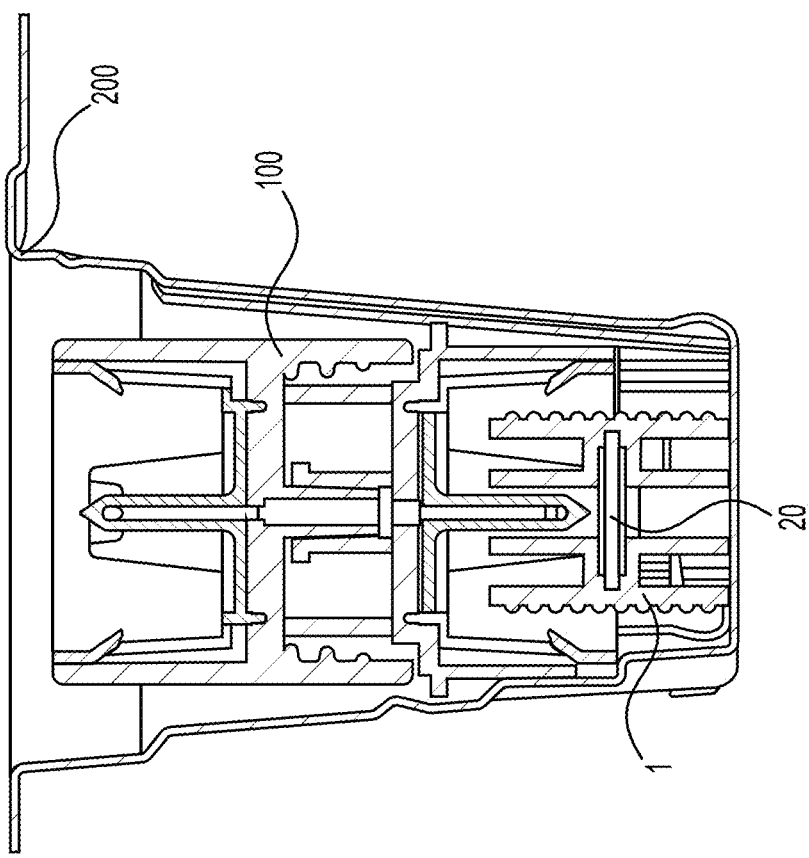
FIG. 16 shows a cross-section of the female-female adapter nested in the reconstitution device package.
Figure 18:
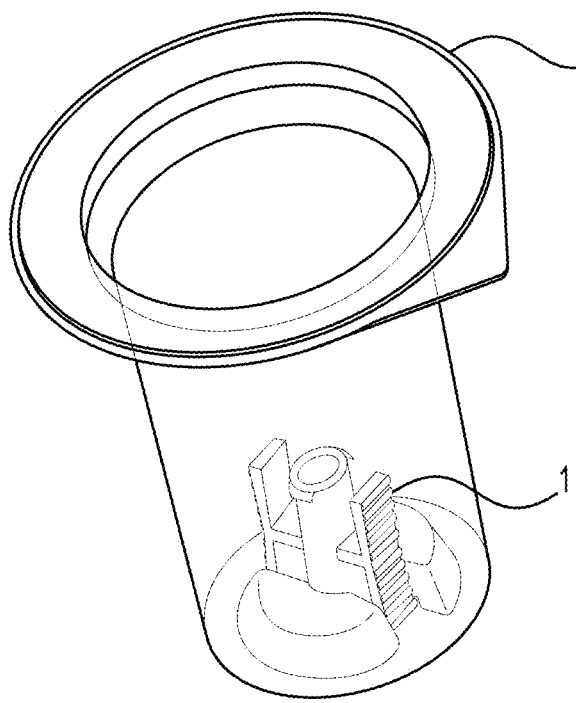
FIG. 18 shows the female-female adapter fit into a modified blister pack.
Figure 19:
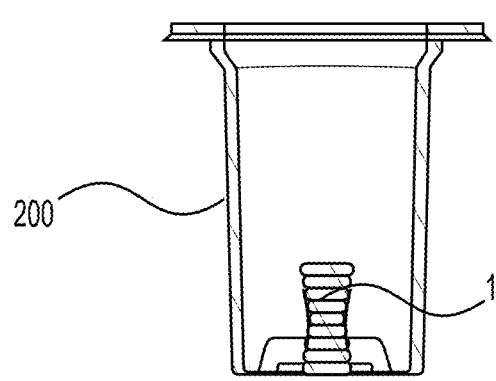
FIG. 19 shows the bow-tie wings of the female-female adapter, allowing snap-fit engagement in the modified blister pack.
Figure 20:
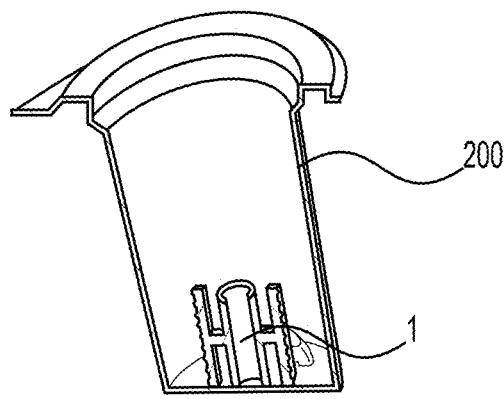
FIG. 20 shows a cross-section of the adapter in the modified blister pack.
Figure 21:
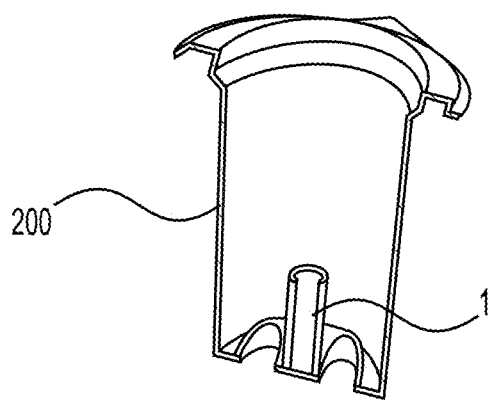
FIG. 21 shows a cross-section of the adapter in the modified blister pack.

FIG. 16 shows a cross-section of the female-female adapter nested in the reconstitution device package.

Figure 17:
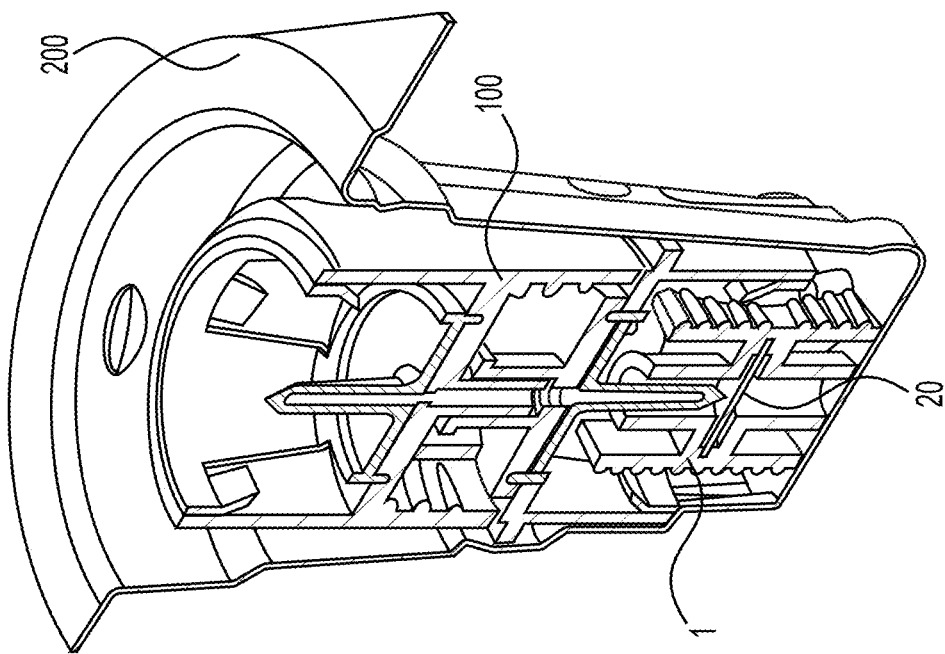
FIG. 17 shows a perspective view of the cross-section of the female-female adapter nested in the reconstitution device package.

FIG. 17 shows a perspective view of the cross-section of the female-female adapter nested in the reconstitution device package.

In certain embodiments, as shown in FIGS. 11-17, the filter 20 is disposed within an expanded central portion 25 of the central lumen. In such embodiments, the filtration area may be about 20 times larger and have a filtration area of about 1 cm2, with the filter captured between two molded pieces of a female-female adapter. Larger surface area enhances particle removal capacity with reduced shear force and fluid flow resistance, which would benefit cases such as sensitive or higher viscosity biologics.

Certain aspects of the invention further comprise a sterile package. The sterile package comprises the reconstitution device and the female-female adapter. In the package, the female-female adapter is arranged in a space between the reconstitution device and an inside surface of the package, the wings releasably interlocking with the inside surface of the package. In some embodiments, the package is a blister pack.

Figure 6:
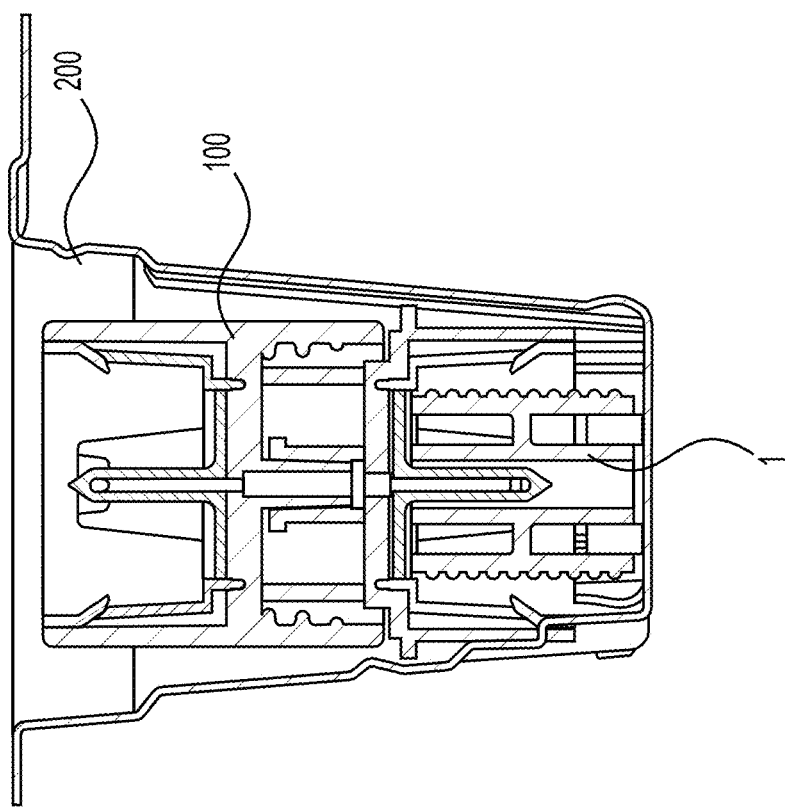
FIG. 6 shows a cross-section of the female-female adapter nested in the reconstitution device package.
Figure 8:
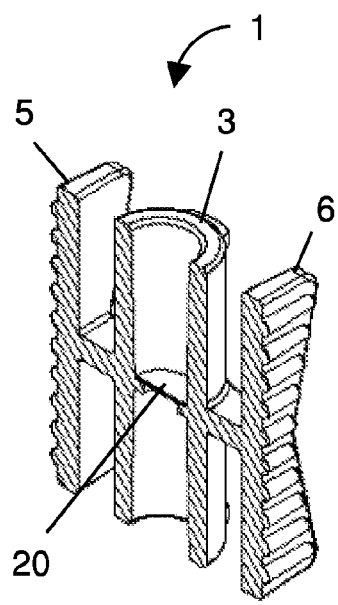
FIG. 8 shows a perspective view of the cross-section of an embodiment of the female-female adapter.
Figure 9:
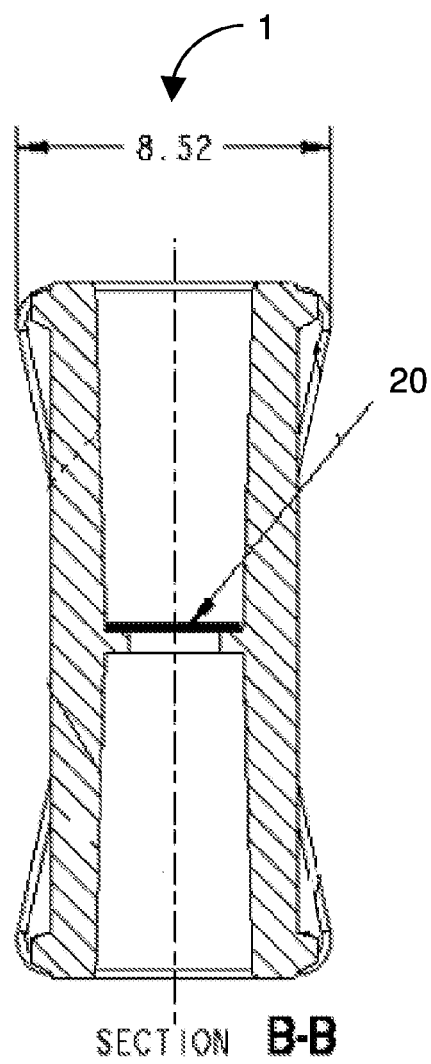
FIG. 9 shows a cross-section of a side view of the female-female adapter.

FIG. 6 shows a cross-section of the female-female adapter 1 nested below the reconstitution device 100 in the reconstitution device package 200.

Figure 7:
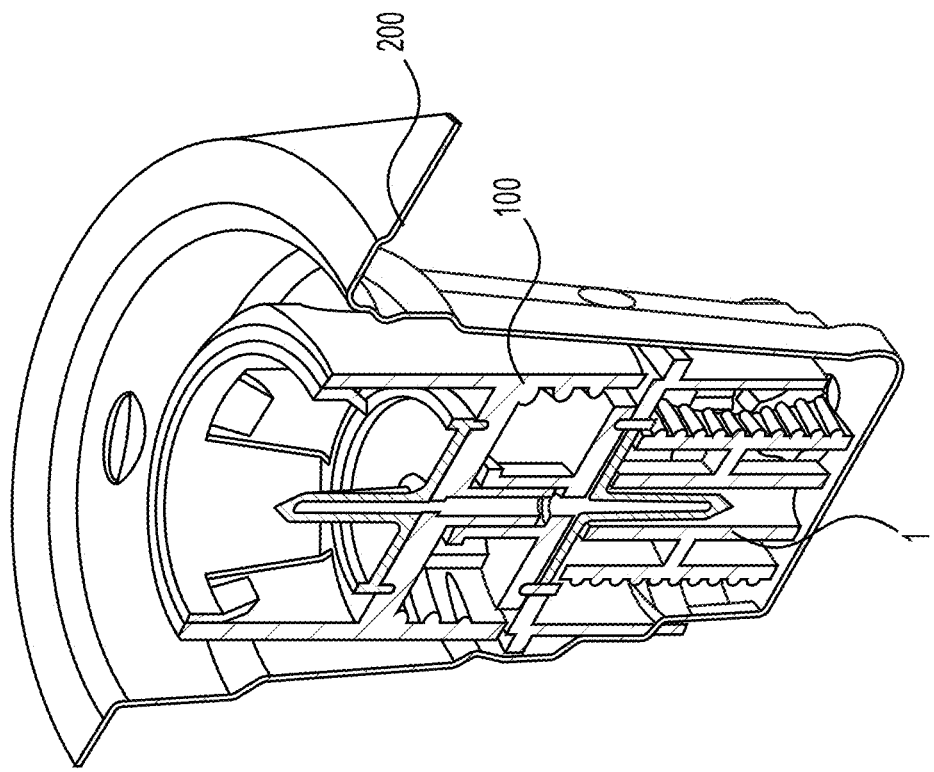
FIG. 7 shows a perspective view of the cross-section of the female-female adapter nested in the reconstitution device package.

FIG. 7 shows a perspective view of the cross-section of the female-female adapter 1 nested in the reconstitution device package 200.

FIG. 16 shows a cross-section of the female-female adapter with filter 20 nested in the reconstitution device package.

Figure 10:
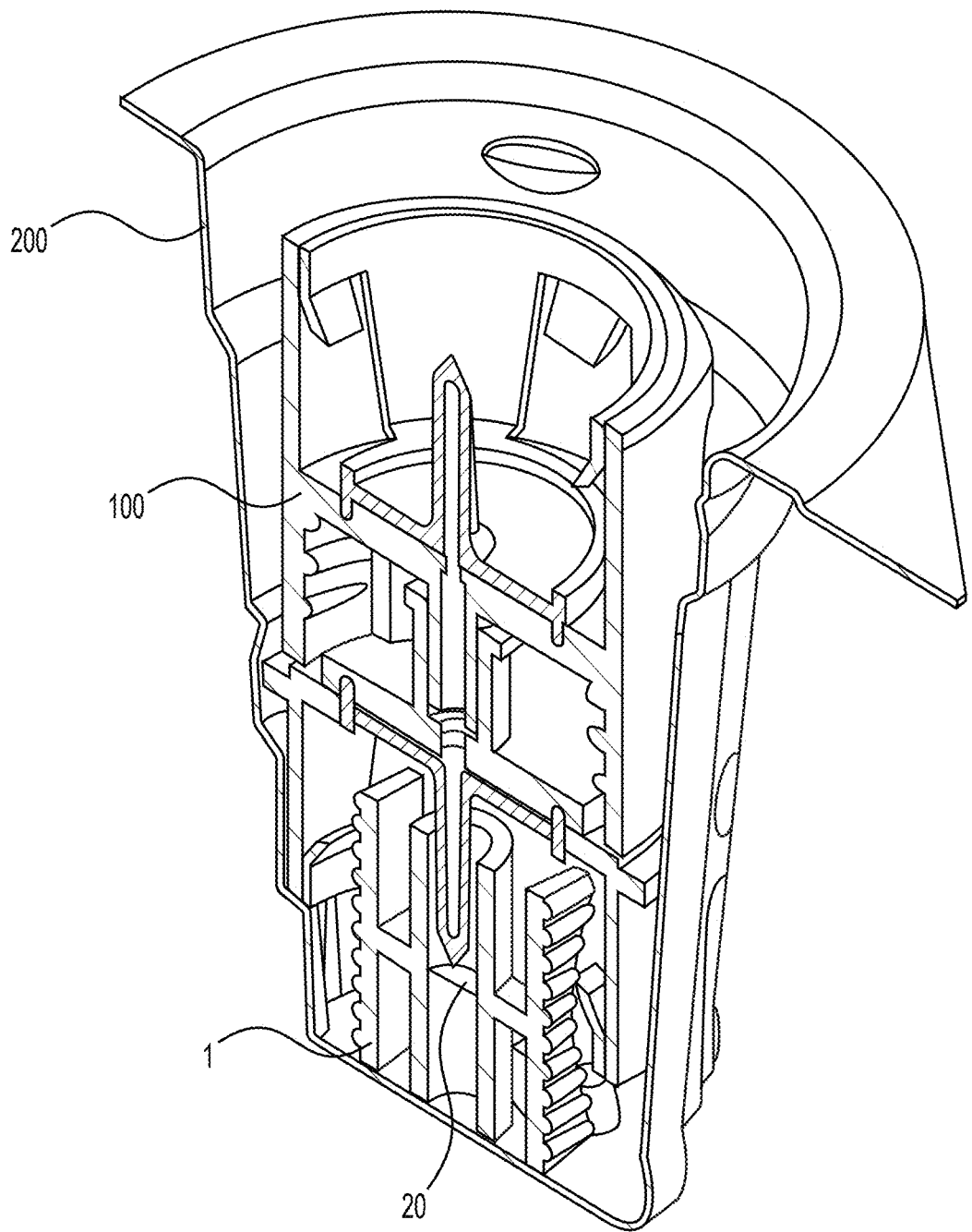
FIG. 10 shows a perspective view of the cross-section of the female-female adapter nested in the reconstitution device package.

FIG. 10 and FIG. 17 show a perspective view of the cross-section of the female-female adapter with filter 20 nested in the reconstitution device package.

FIG. 18 through FIG. 21 show the female-female adapter 1 fit into a modified blister pack 200.

Figure 22:
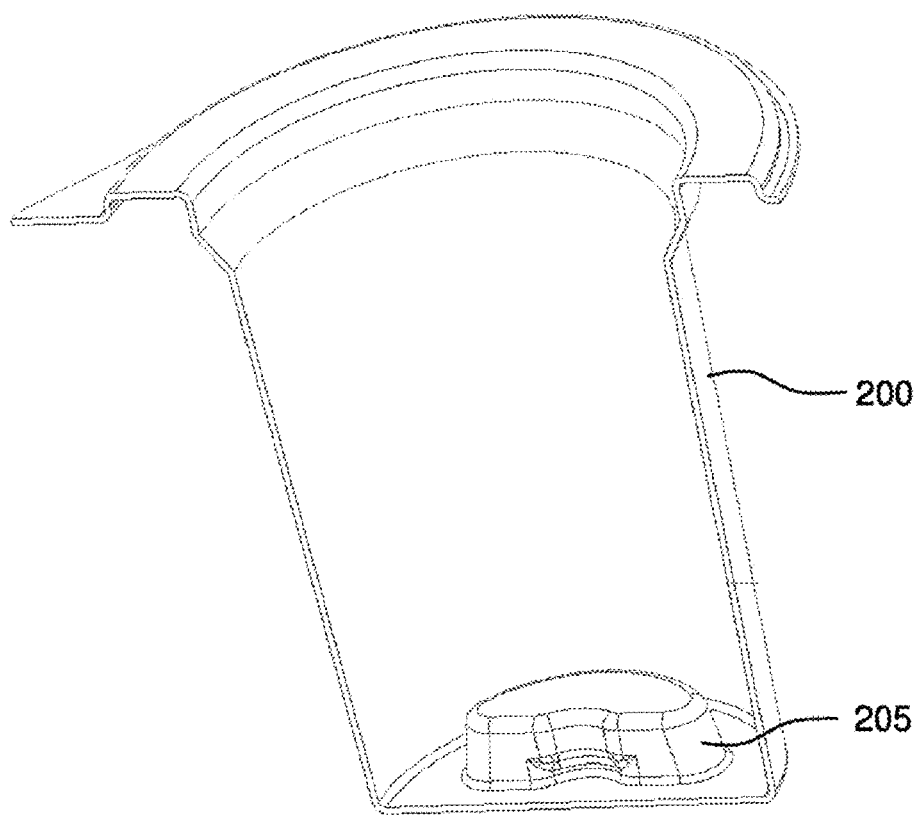
FIG. 22 shows a cross-section of the modified blister packaging, wherein the blister pack has dual undercuts to engage both Luer lugs and bow-tie wings.
Figure 23:
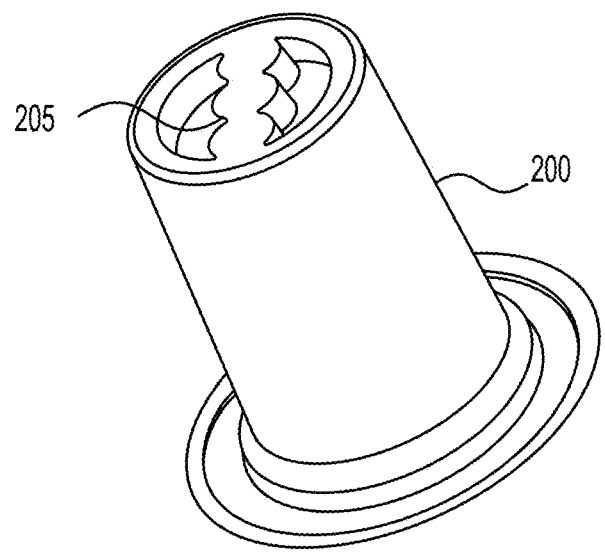
FIG. 23 shows the adapter retention features formed in the base of the modified blister pack, which resist rotation when a syringe is torqued on, resist axial displacement of the adapter during distribution, and allows disengagement of the adapter with a light pull.

FIG. 22 and FIG. 23 show the modified blister pack. The blister pack may have adapter retention features 205, such as dual undercuts, to engage both Luer lugs and bow-tie wings. The adapter retention features 205 formed in the base of the modified blister pack have sufficient stiffness to resist rotation of the adapter when a syringe is torqued on, resist axial displacement of the adapter during distribution, and allows disengagement of the adapter with a light pull. Further, the deep capture location of the female-female adapter within the blister pack also prevents touch contamination. Users access the adapter by threading a syringe and pulling, rather than direct handling to extract the adapter.

The nested positioning of the adapter aids retention in the blister pack within the undercuts during shipping. The adapter cannot vibrate up and away from undercuts during shipping due to the recon device floor immediately above the adapter. Further, stable upright positioning of the female-female adapter within the blister pack allows easy connection and extraction by syringe, with blister pack side walls preventing risk of touch contamination of fluid path. The adapter is symmetrical to reduce orientation dependency during assembly to the blister. Furthermore, the degree of engagement between the wings and blister undercuts in the packaging may be increased for stronger retention or decreased for easier removal from the packaging.

In certain embodiments, a female-female adapter is beneath the reconstitution device and nested partially inside of the reconstitution device in the blister pack. The spike of the reconstitution device fits within the inside diameter of the adapter fluid path. Fit with the blister pack is improved when the wings have a bow-tie configuration. Ribs or ridges 7 on the outer surfaces of the wings improve handling when the user disconnects.

Users only extract the female-female adapter when necessary, such as when a diluent transfer issue arises. No standalone package or label is required for the female-female adapter. Users access the female-female adapter by threading a syringe into the female-female adapter and pulling the syringe and attached female-female adapter from the blister pack with minimal effort. This low-cost addition to the blister pack may be sterilized by the same gamma or ethylene oxide (EtO) sterilization cycle as the reconstitution device.

In certain embodiments, the adapter may be brightly opaque colored to be clearly visible inside a translucent blister pack to increase visibility once the reconstitution device is removed from the blister pack. In other embodiments, a distinct color makes the female-female adapter easily referenceable in the instructions for use included with the reconstitution device or reconstitution product. In another embodiment, use of a white/clear (translucent) resin allows the female-female adapter to blend in with the reconstitution device blister pack. In another embodiment, use of a clear (translucent) resin female-female adapter allows for better visualization of the flow path for the female-female adapter.

In an embodiment, the present invention provides a system for a reconstitution product. The system comprises a reconstitution device and a female-female adapter. The system comprises a package comprising the reconstitution device and the female-female adapter. Within the package, the female-female adapter may be arranged in a space between the reconstitution device and an inside surface of the package, the wings releasably interlocking with the inside surface of the package. In certain embodiments, the package is a blister pack. In some embodiments, the package and contents are sterilized. In an aspect of the invention, the female-female adapter is attached without touch contamination. The ridges on the wings provide an area for a user to securely grip the adapter without contaminating the ends of the central lumen.

Figure 24:
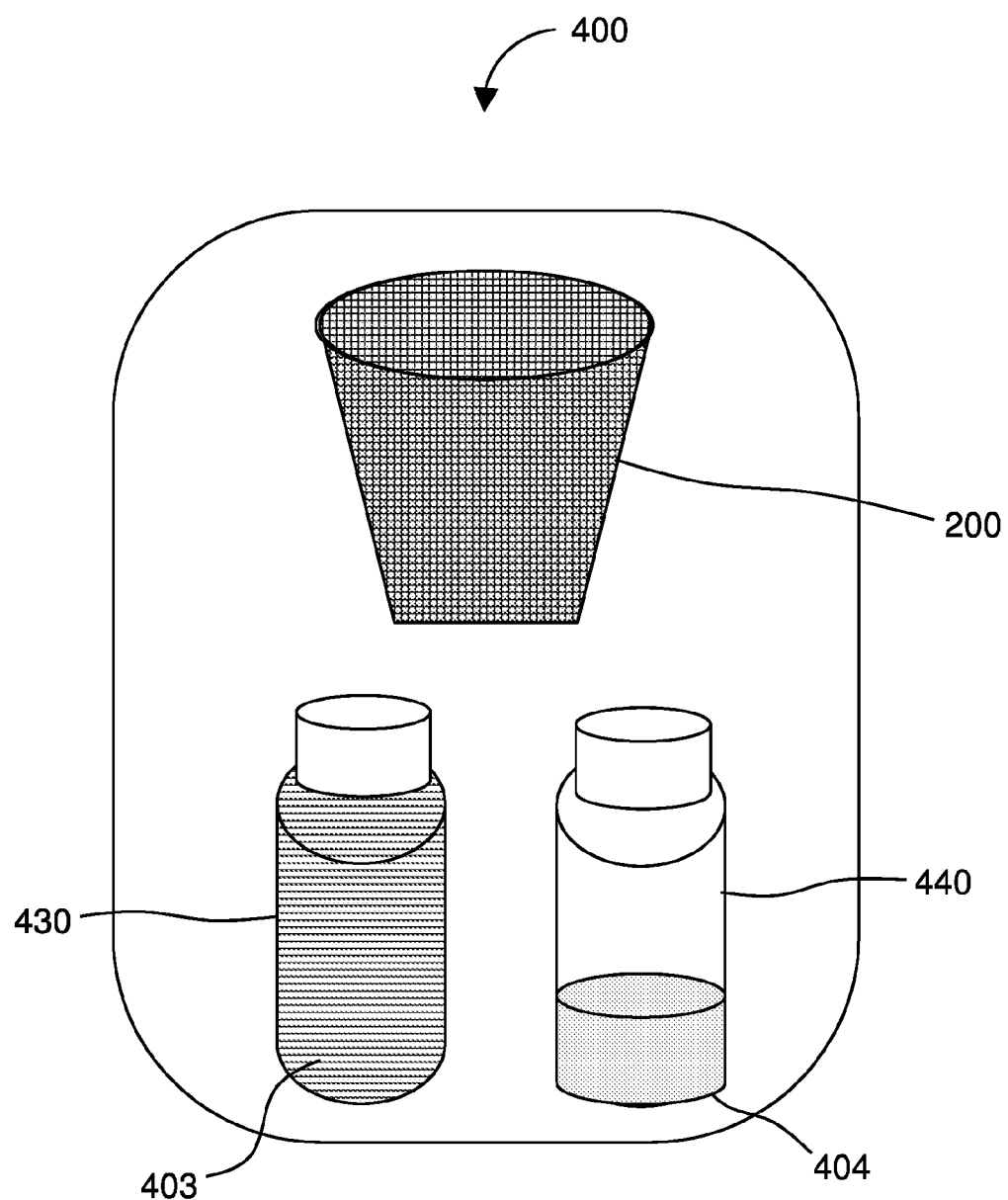
FIG. 24 shows an embodiment of a system or kit according to the present invention.

In certain embodiments, the system further comprises a reconstitution product. A system or kit 400 is shown in FIG. 24 and includes a reconstitution product (a diluent vial 430 containing a diluent 403 and a lyophilized powder vial 440 containing a lyophilized powder 404) and a reconstitution device package 200 comprising a reconstitution device and female-female adapter. Embodiments showing the reconstitution device package 200 comprising a reconstitution device 100 and a female-female adapter 1 and the arrangement therein are shown in FIGS. 6, 7, 10, 16, and 17. The reconstitution device comprises a first component 450 and a second component 460, the first component and the second component capable of disconnecting. Examples of reconstitution devices with center-disconnecting double spikes include NEXTARO® and MIX2VIAL®. The female-female adapter comprises wings extending from a central lumen, the female-female adapter having a first end connectable with a male nozzle of a syringe and a second end connectable with a male nozzle of the first component or the second component. The reconstitution product comprises a first vial 430 comprising a diluent 403 and a second vial 440 comprising a lyophilized powder 404, the first vial 430 for connecting to the first component 450 and the second vial 440 connecting to the second component 460 (FIG. 25).

In certain embodiments, the female-female adapter has female Luer lock fitting geometry on both ends of the central lumen of the female-female adapter to provide security when docking or threading the female-female adapter to male Luer lock fittings.

In certain embodiments, the male nozzle is a Luer lock.

Figure 26:
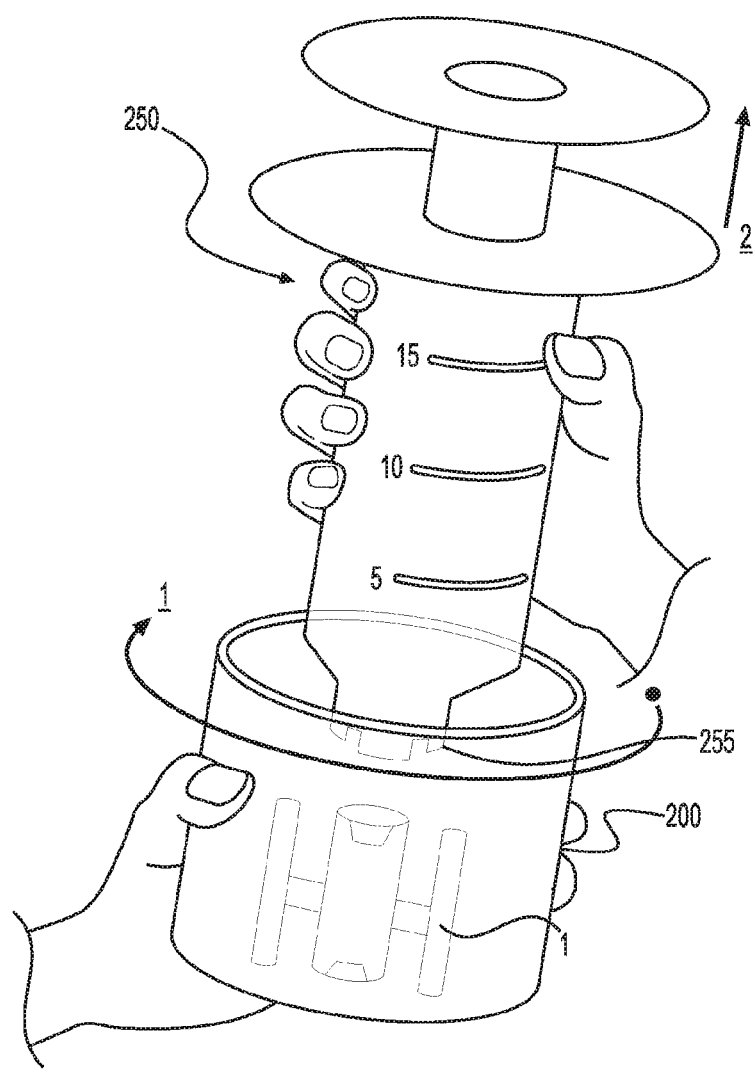
FIG. 26 shows connection of the adapter with a syringe having a male Luer lock nozzle.

FIG. 26 shows connection of a syringe 250 to the adapter 1. The Luer lock male nozzle 255 of the syringe 250 is threaded into the adapter 1 while the adapter is in the package 200. The syringe may have graduated markings 275.

Figure 27:
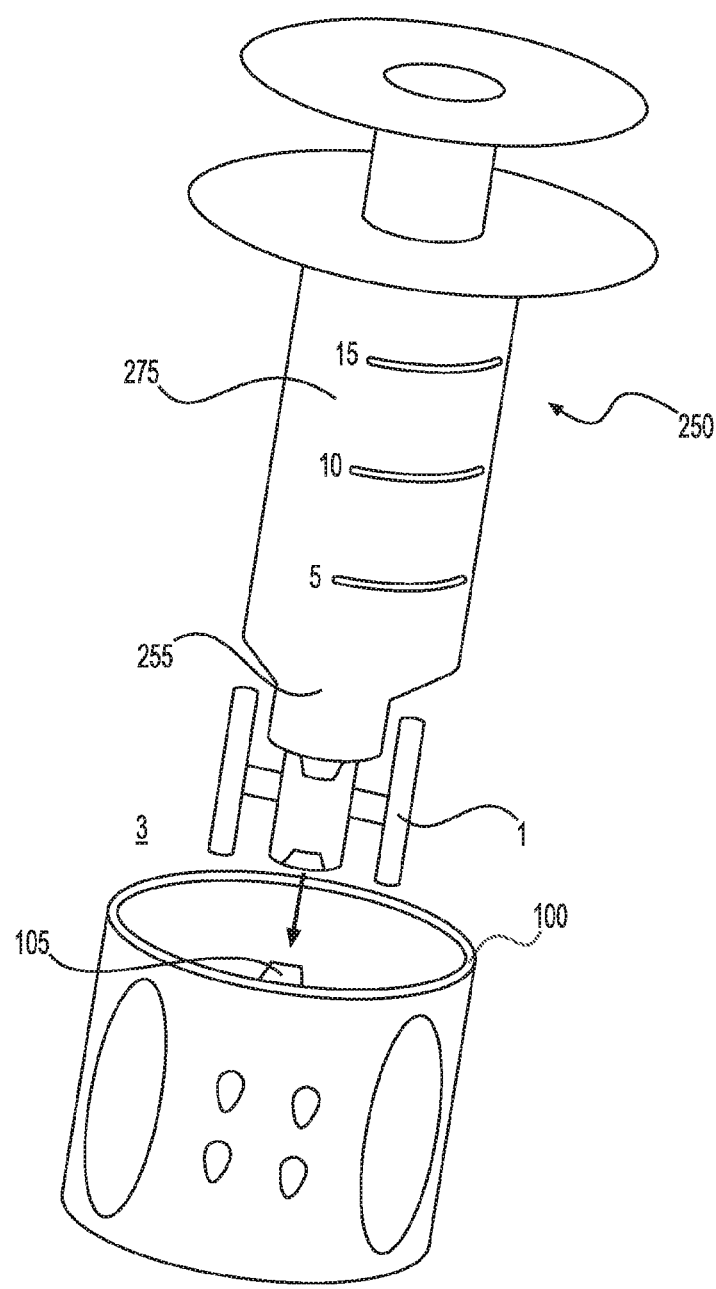
FIG. 27 shows connection of the adapter, which is attached to a male Luer lock nozzle of a syringe, to a male nozzle of a reconstitution device.

FIG. 27 shows connection of the adapter 1, which is attached to a male Luer lock nozzle 255 of a syringe 250, to a male nozzle 105 of a reconstitution device 100. In certain embodiments, to explain how and when to access the adapter and the intended use of the adapter, a short description and simple illustrations may be added to instructions for use for either the reconstitution device or the biologic product. For example, instructions may provide steps for using the female-female adapter to recover from an error that prevented diluent transfer. Step (1) Firmly twist syringe into the adapter. Step (2) pull out from package. Step (3) the adapter allows manually moving of fluid in or out of the reconstitution device by syringe. Steps 1 and 2 are shown in FIG. 26, and Step 3 is shown in FIG. 27. Remove and discard the female-female adapter when fluid has been removed from the reconstitution device.

The present invention provides methods of using a female-female adapter for recovery of reconstituted product. The female-female adapter allows recovery from incorrect docking of the spike for the diluent vial into the product vial. The female-female adapter allows recovery from docking the product vial with an incorrect orientation, such as spiking the product vial when it is not flat on a surface. In an embodiment, the present invention provides methods of using a female-female adapter to reconstitute a lyophilized powder.

In one example, the user may have connected the reconstitution device to an incorrect vial, such as connecting the powder component of the reconstitution device to the diluent vial.

Figure 28:
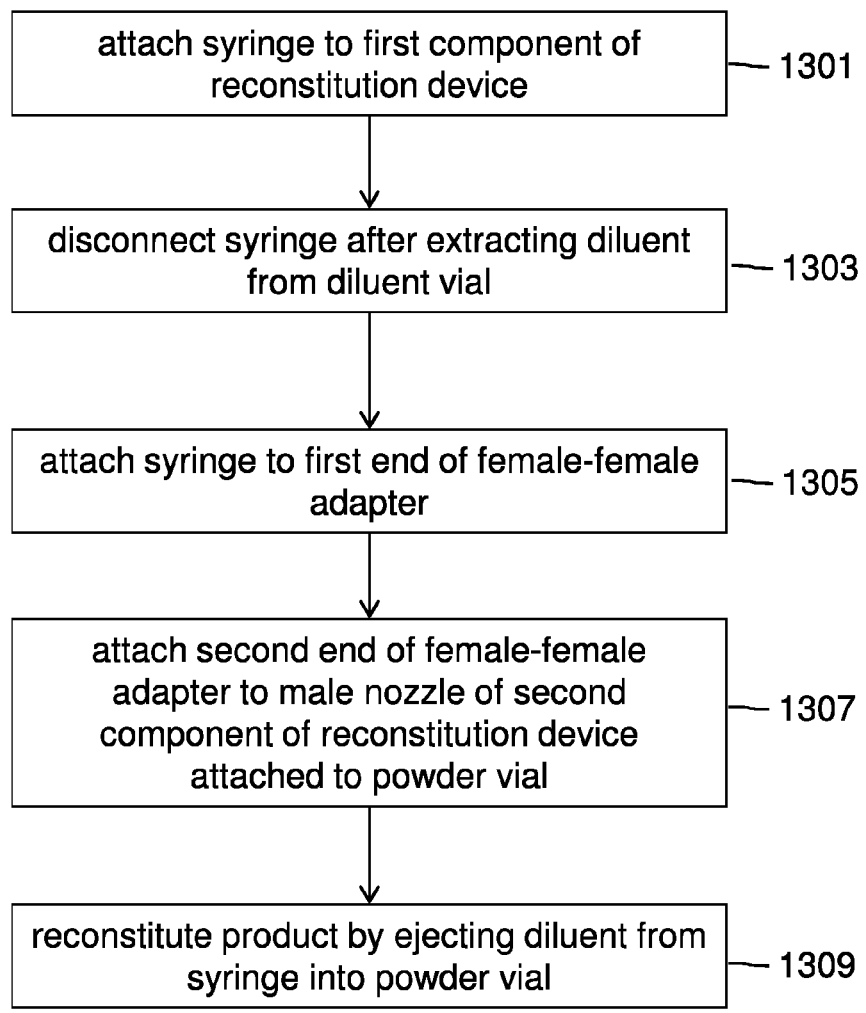
FIG. 28 is a flowchart according to an embodiment of the invention.

FIG. 28 is a flowchart according to an embodiment of the invention. As shown, a syringe is attached to a first component of a reconstitution device 1301 and the syringe is disconnected after extracting a diluent from a first vial 1303. A lyophilized powder is reconstituted by attaching the male nozzle of the syringe to a first end of a female-female adapter 1305, attaching a second end of the female-female adapter to a male nozzle of a second reconstitution device attached to a second vial comprising the lyophilized powder 1307, and ejecting the diluent into the second vial 1309. In certain embodiments of the methods, the syringe has a male Luer lock nozzle.

In another example, the user may have incorrectly oriented the lyophilized powder vial when connecting the powder vial to the reconstitution device, i.e., turning the powder vial upside down and lifting it off of a surface to connect the powder vial to the reconstitution device sitting on the surface.

Figure 29:
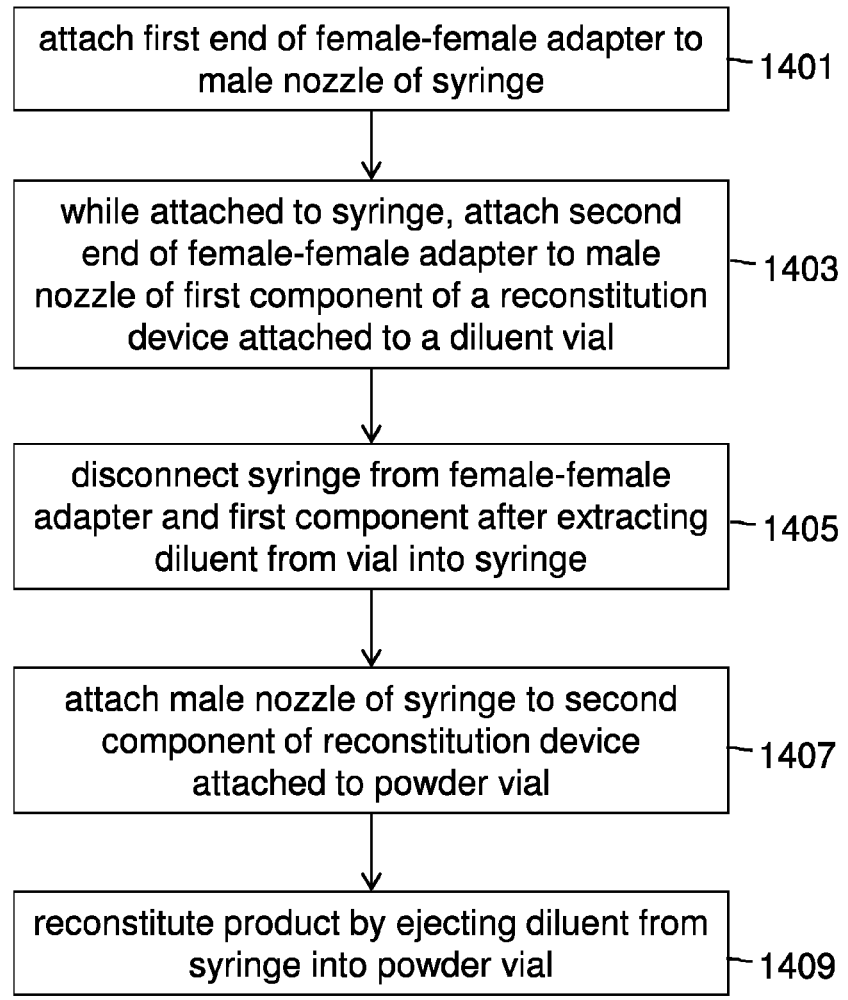
FIG. 29 is a flowchart according to an embodiment of the invention.

FIG. 29 is a flowchart according to an embodiment of the invention. As shown, a first end of a female-female adapter is attached to a male nozzle of a syringe 1401. In certain embodiments of the methods, the syringe has a male Luer lock nozzle. A second end of the female-female adapter is attached to a first component of a reconstitution device attached to a first vial 1403, and the syringe is disconnected from the female-female adapter after extracting a diluent from the first vial into the syringe 1405. A lyophilized powder is reconstituted by attaching the male nozzle of the syringe to a second component of the reconstitution device attached to a second vial comprising the lyophilized powder 1407 and ejecting the diluent into the second vial 1409.

FIG. 30 through FIG. 34 show the use of the female-female adapter with a MIX2VIAL® reconstitution device.

Figure 30:
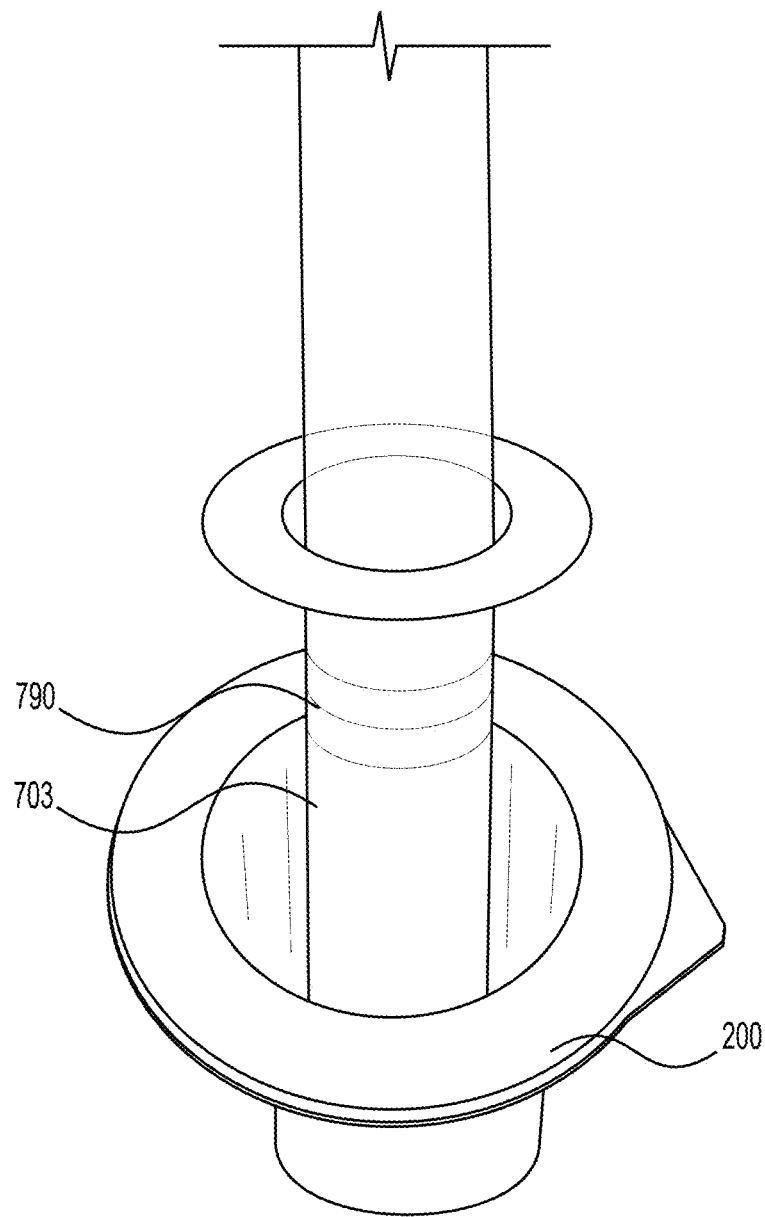
FIG. 30 shows a syringe extracting the adapter from a package.

FIG. 30 shows a syringe 790 extracting the female-female adapter 1 from a package 200. The syringe 790 is filled with diluent 703 from a diluent vial 730. A first component 750 of the reconstitution device is attached to the diluent vial 730.

Figure 31:
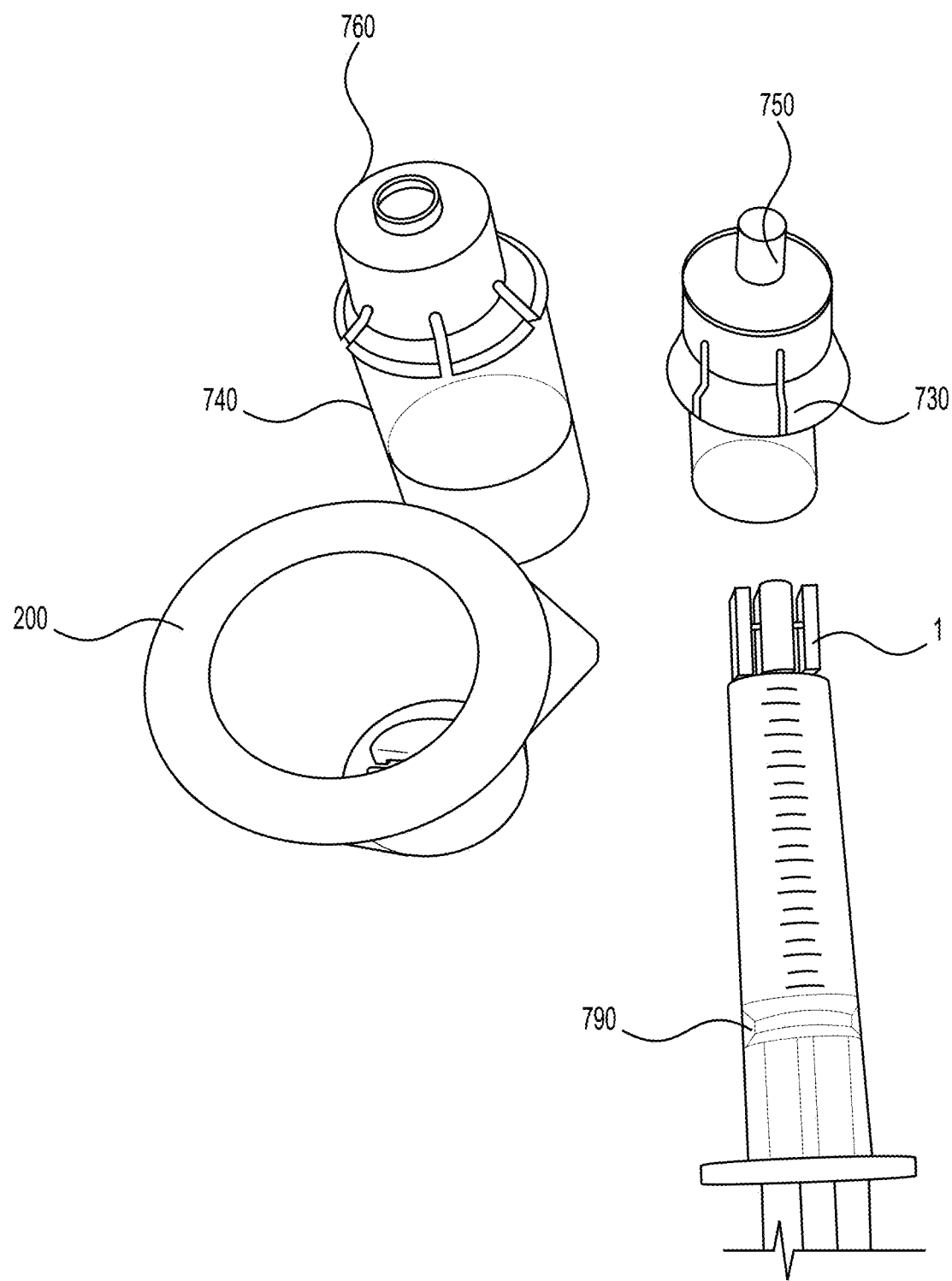
FIG. 31 shows the adapter attached to the syringe and ready to connect to a male nozzle.

FIG. 31 shows the female-female adapter 1 attached to the syringe 790 and ready to connect to a male nozzle.

FIG. 32 shows a user 775 manually transferring diluent 703 from the syringe 790 into a powder vial 740 containing lyophilized powder 704. A second component 760 of the reconstitution device is attached to the powder vial 740.

FIG. 33 shows the female-female adapter 1 docked to the male Luer fitting 765 of the second component 760 of the MIX2VIAL® reconstitution device, as would appear when the user has removed the syringe following product aspiration from the vial.

The female-female adapter may allow syringe to syringe connections, and therefore transfer of fluid between syringes. Such a strategy may be used to pool multiple doses into a single syringe. The strategy may further be used to transfer fluid to a smaller barrel syringe with greater dosing precision and tighter graduation markings. The adapter may be positioned in an upright manner in a package, such as a blister pack, containing a multi-chambered syringe, such as a dual-chambered syringe, and a plunger for the multi-chambered syringe. In an embodiment, the present invention provides a system for a reconstitution product comprising a reconstitution device and a female-female adapter. The reconstitution device comprises a plunger and a dual-chambered syringe comprising first chamber containing a diluent and a second chamber containing a lyophilized powder. The female-female adapter comprises wings extending from a central lumen. The female-female adapter has a first end connectable with a male nozzle of the dual-chambered syringe a second end connectable with a male nozzle of a syringe.

Figure 34:
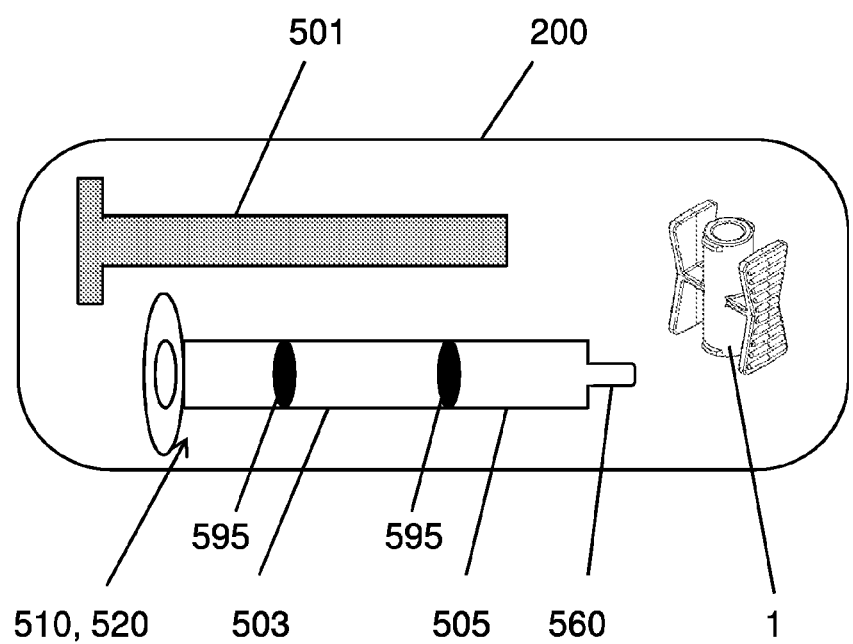
FIG. 34 shows an embodiment where the female-female adapter is packaged with a dual-chambered syringe and plunger for the syringe.

FIG. 34 shows an embodiment where the female-female adapter 1 is included in a package 200 with a dual-chambered syringe 510, 520 and plunger 501 for the dual-chambered syringe. The chambers of the dual-chambered syringe may be separated by any suitable separation, such as a valve or seal 595. This offers an advantage for users who need the ability to pool multiple doses from pre-filled syringes or multi-chambered syringes such as Lyo-Ject® (a registered United States trademark, manufactured by Vetter Pharma International GmbH). This also allows transfer of a full or partial dose to an alternate syringe, such as one that offers more delivery precision by smaller diameter barrel or finer graduation marks. A further advantage is to allow filtration of a fluid from multi-chambered syringes when the filter 20 is disposed in the central lumen 3, as shown in FIGS. 8-17.

FIG. 35 through FIG. 38 show a dose combination process. Within a dual-chambered syringe 510, 520, a plunger 501 pushes through the valve or seal 595 and mixes a first chamber, which contains a diluent 503, and a second chamber, which contains a lyophilized powder 505, to form a dose 515, 525. In the dose combination method, a first end of a female-female adapter is attached to a male nozzle of a syringe. A first dose 515 and a second dose 525 are combined 555 in the syringe by an extraction process. The extraction process comprises extracting the doses from two multi-chambered syringes 510, 520. A second end of the female-female adapter is attached to a male nozzle of a first multi-chambered syringe 510, and the female-female adapter 1 is disconnected from the first multi-chambered syringe 510 after extracting and collecting the first dose 515 in the syringe. The second end of the female-female adapter is attached to a male nozzle of a second multi-chambered syringe 520, and the female-female adapter 1 is disconnected from the second multi-chambered syringe 520 after extracting and collecting the second dose 525 in the syringe 500.

The invention may be embodied in other specific forms without departing from the spirit or essential characteristics thereof. The foregoing embodiments are therefore to be considered in all respects illustrative rather than limiting on the invention described herein.

What is claimed is:

1. A method of using a female-female adapter including a central lumen having a first end and a second end to reconstitute a lyophilized powder, the method comprising:
    attaching a first end of a female-female adapter to a male nozzle of a syringe, the female-female adapter comprising wings extending parallel to the central lumen, each wing having a slat with a bow-tie shape, wherein each slat has an upper widest portion and a lower widest portion, and a narrowed middle portion between them;
    pulling the female-female adapter axially, with the syringe and without touching the female-female adapter, such that the slats disengage from dual undercuts in a packaging, wherein each undercut engages the slat proximate the narrowed middle portion such that the lower widest portion of each slat is positioned below the respective undercut and the upper widest portion of each slat is positioned above the respective undercut;
    removing the female-female adapter, with the female-female adapter attached to the syringe, from the packaging;
    attaching a second end of the female-female adapter to a first component of a reconstitution device attached to a first vial, extracting a diluent from the first vial into the syringe;
    disconnecting the syringe from the female-female adapter without touching the female-female adapter; and
    reconstituting a lyophilized powder by attaching the male nozzle of the syringe to a second component of the reconstitution device attached to a second vial comprising the lyophilized powder and ejecting the diluent into the second vial.

2. The method of claim 1, wherein the syringe has a male Luer lock nozzle.

3. The method of claim 1, wherein the female-female adapter is attached without touch contamination.

4. A system comprising:
    a female-female adapter comprising:
        a central lumen having two ends, an inner surface, and an outer surface, the two ends opposite each other in a longitudinal direction, the two ends each capable of interlocking with a male end of a nozzle, and the central lumen having a central portion in the longitudinal direction; and
        wings extending from the central portion and located at points opposite each other around a circumference of the central lumen, each wing forming a slat parallel to the central lumen, the slat having a first end and a second end wider than a narrowed middle section of the slat thereby forming a bow-tie shape; and
    a packaging comprising a base, the base comprising dual undercuts, wherein each undercut is sized and shaped to engage a corresponding wing proximate the narrowed middle section such that a lower widest portion of the slat is positioned below the respective undercut, and an upper widest portion of the slat is positioned above the respective undercut, and wherein the female-female adapter is retained in an upright vertical orientation wherein the wings extend from the base in the longitudinal direction.

5. The system of claim 4, wherein the wings of the female-female adapter further comprise ridges on a surface of the slat exterior to the central lumen.

6. The system of claim 4, wherein the male end of the nozzle of the female-female adapter is a Luer lock.

7. The system of claim 4, wherein the female-female adapter further comprises a filter disposed in the central lumen at the central portion and perpendicular to the longitudinal direction of the central lumen.

8. The system of claim 7, wherein the filter of the female-female adapter is welded to the central lumen of the female-female adapter.

9. The system of claim 4, wherein the packaging further comprises a reconstitution device arranged within the packaging.

10. The system of claim 9, wherein the reconstitution device comprises a first component and a second component, each component comprising a base and a spike, each spike extending perpendicularly from a plane of the corresponding base.

11. The system of claim 10, wherein the female-female adapter is positioned within the packaging beneath the reconstitution device and is partially nested within the reconstitution device such that one of the spikes of the reconstitution device is aligned with and extends into the central lumen of the female-female adapter.

* * * * *